United States Patent [19]

Kataoka

[11] 4,102,079

[45] Jul. 25, 1978

[54] METHOD OF BREEDING NEW VARIETIES OF THE FIRST FILIAL GENERATION PLANT

[76] Inventor: Setsuo Kataoka, 2-10-4 Shimizu, Suginami-Ku, Tokyo, Japan

[21] Appl. No.: 781,328

[22] Filed: Mar. 25, 1977

[30] Foreign Application Priority Data

Jul. 5, 1976 [JP] Japan .................................. 51/78902

[51] Int. Cl.$^2$ ............................................ A01H 1/02
[52] U.S. Cl. .................................. 47/58; 47/DIG. 1
[58] Field of Search ............................ 47/58, DIG. 1

[56] References Cited

PUBLICATIONS

Breeding Field Crops, Poehlman, 1959, Holt, Rinehart & Winston, N.Y., pp. 40–44 relied on.

*Primary Examiner*—Robert E. Bagwill
*Attorney, Agent, or Firm*—Sherman & Shalloway

[57] ABSTRACT

A method of breeding new varieties of a first filial generation plant is disclosed. The first filial generation plant is obtained by crossing an allopolyploidy plant as female with several species in Brassica genus as male. The allopolyploidy plant is composed of an interspecific plant or reciprocal cross formed of *Brassica olesacea* and another species in Brassica genus.

4 Claims, 21 Drawing Figures

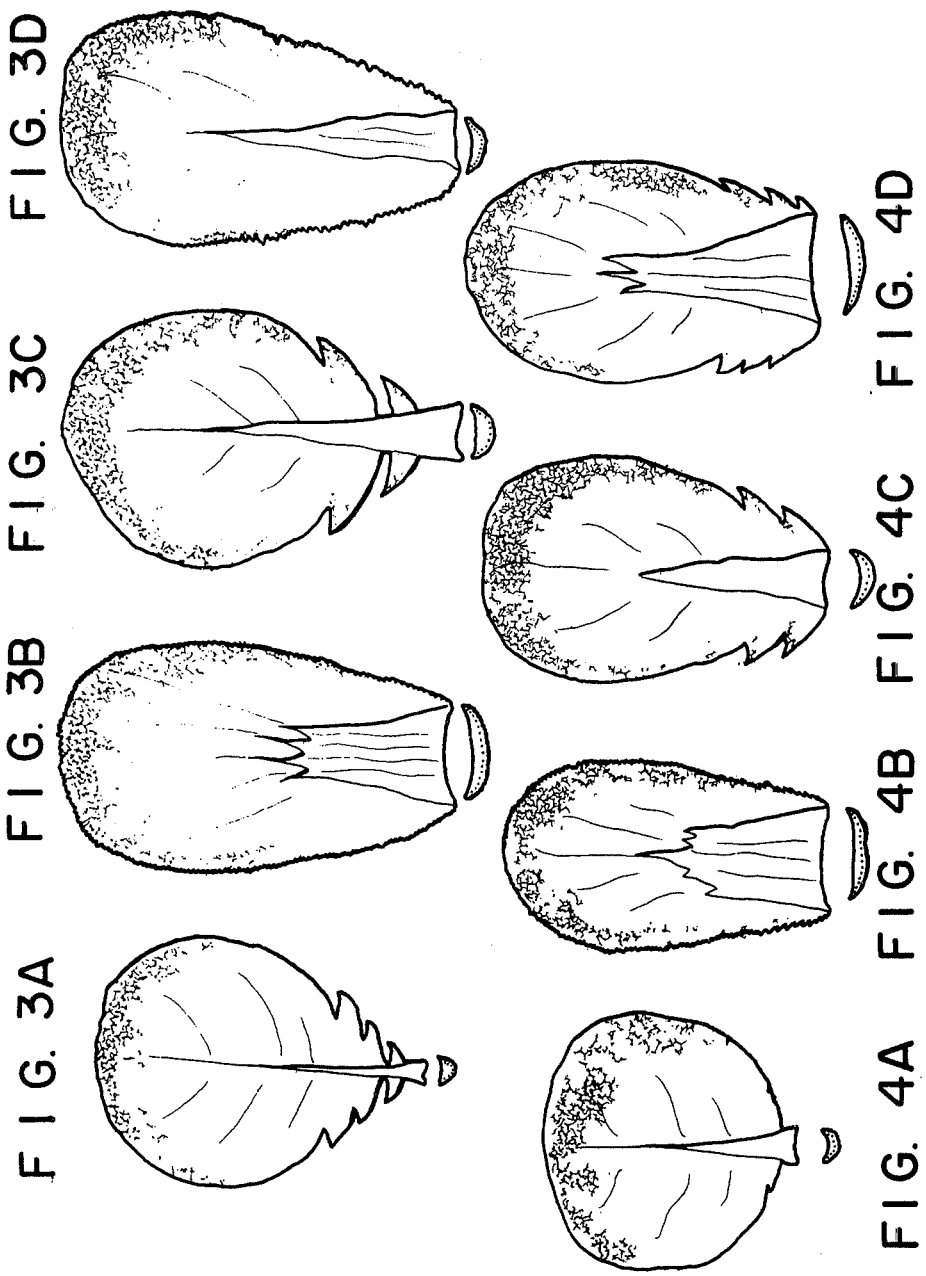

FIG. 5A
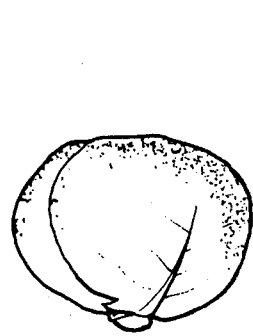
FIG. 5B
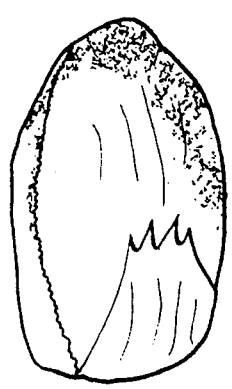
FIG. 5C
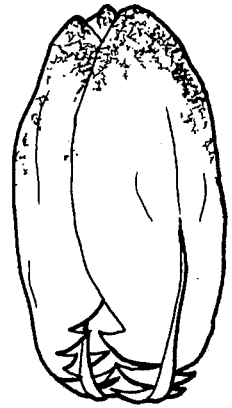
FIG. 5D1
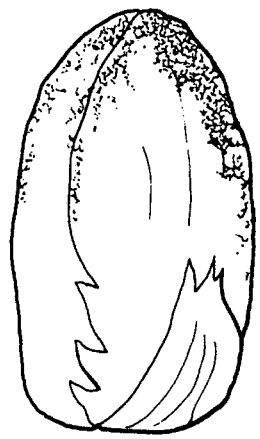
FIG. 5D2

METHOD OF BREEDING NEW VARIETIES OF THE FIRST FILIAL GENERATION PLANT

BACKGROUND OF THE INVENTION

This invention relates to a method of breeding new varieties of a first filial generation plant.

The term "Brassica oleracea" shall be understood to mean leaf vegetables having genome CC and containing Brassica oleracea L, for example, head cabbage, kale, Japanese ornament kale, brussels-sprouts, kohlrabi, cauliflower, broccoli, kairan and the like.

The term "Brassica genus" shall be understood to mean leaf vegetables having genome AA and/or BB, such as leaf vegetables listed in the following Table 1, that is, Brassica napus and the other 10 leaf vegetables, for example, Brassica nigra, Brassica alba and the like.

An allopolyploidy plant (genome CCAA or AACC) has heretofore been bred by Dr. Sadao Nishi et al belonging to the Department of Agriculture and Forestry, Vegetable Testing Plant by treating an interspecific hybrid (genome AC) composed of common cabbage (genome CC) and Chinese cabbage (genome AA) with colchicine etc. so as to increase twofold chromosome number thereof. The allopolyploidy plant thus bred is referred to as Hakuran.

The Hakuran thus bred has a number of drawbacks. In the first place, the Hakuran is insufficient in compact head formation and small in seed yield. Secondly, even though selection is repeatedly effected, it is difficult to improve its uniformity. Third, it is difficult to utilize the Hakuran in vegetable culture. Finally, the Hakuran is mostly self-incompatible.

Such self-incompatibility of the Hakuran is reported by Mr. Kuriyama in his article, "Study on Vegetables", published in 1976 by the Department of Agriculture and Forestry, Vegetable Testing Plant.

Attempts have been made to eliminate the self-incompatibility of the Hakuran by selection, but none of these attempts has led to a satisfactory solution which can be used in practice since the Hakuran is still difficult to make self-compatible and also difficult in seed production.

It is possible to effect seed production of a first filial generation plant, i.e., $F_1$ hybrid obtained by crossing one Hakuran with another Hakuran. In this case, the Hakurans having bad uniformity are crossed with each other, and as a result, the $F_1$ hybrid plant thus obtained becomes more degraded in uniformity, thus increasing difficulty in utilizing it in vegetable culture.

The reasons why the polyploid inclusive of the allopolyploid has a bad uniformity are as follows. The gene number of the polyploid is increased by a multiple "a" of the monoploid prior to polyploidy thereof in response to the chromosome number. Difficulty in improving uniformity by selection is proportional to an increase of the gene number.

There are natural allopolyploids such, for example, as Brassica napus (genome AACC, chromosome number $2n = 38$) and Brassica juncea (genome AABB, chromosome number $2n = 36$). These natural allopolyploids, however, have been subjected to selection for hundred years, so that these natural allopolyploids have a good uniformity and hence are self-compatible.

On the contrary, the Hakuran is a new plant which has been bred for only 10 years, so that it is inevitable that the Hakuran has a bad uniformity. As a result, it is difficult to quickly improve the uniformity of the Hakuran by selection. Thus, measures must be taken to cross the Hakuran with a plant whose chromosome number is smaller than that of the Hakuran so as to reduce the chromosome number of the Hakuran and to utilize as the plant to be crossed with the Hakuran, a line having a high purity, uniformity and least possible variation. In addition, it is desirous that the seed yield is more than 10% that of the conventional common cabbage or Chinese cabbage for the purpose of selling the seed.

(1) CROSSING FOR IMPROVING UNIFORMITY

In order to reduce the chromosome number of the above described Hakuran (genome CCAA, chromosome number $2n = 38$), the Hakuran is crossed with an A genome group constituting an original genome (Chinese cabbage, kale type Chinese cabbages and turnip, etc.), and having a chromosome number $n = 10$, $2n = 20$ to obtain a $B_1F_1$ hybrid (genome CAA) which is a one time recurrent back-crossing of the A genome to the AC genome. Thus, the somatic chromosome number (which corresponds to $2n$) becomes 29 which is considerably smaller than the chromosome number 38 of the Hakuran.

The A genome group has mostly been subjected to selection from antiquity and has further been subjected to pure line selection and hence has an extremely high uniformity. The same is true for the C genome group.

As common cabbage, which has the C genome, contains more recessive genes than the Chinese cabbage, so the uniformity of the $B_1F_1$ hybrid of genome CAC is inferior to that of the $B_1F_1$ hybrid of genome CAA in head formation.

In addition, a $F_1$ hybrid with broad leafed mustard which is a natural allopolyploid has a slightly reduced chromosome number. For example, $F_1$ hybrid composed of Hakuran (genome CCAA, chromosome number $2n = 38$) and broad leafed mustard (genome AABB, chromosome number $2n = 36$) has genome CAAB, and a somatic chromosome number (which corresponds to $2n$) of 37, which shows that its chromosome number is reduced by only one. But, the broad leafed mustard is a natural allopolyploid which has been subjected to selection for more than several hundred years and hence has a high uniformity. As a result, the $F_1$ hybrid composed of Hakuran and broad leafed mustard becomes higher in uniformity than the Hakuran, but it is inevitable that its complete head formation becomes lost.

SUMMARY OF THE INVENTION

An object of the invention is to provide a method of breeding new varieties of a first filial generation plant obtained by crossing an allopolyploidy plant composed of an interspecific plant or reciprocal cross formed of Brassica oleracea and several other species of the Brassica genus.

Another object of the invention is to provide a method of obtaining new varieties of a first filial generation plant in mass seed production scale and utilizing them in vegetable culture.

An embodiment of the method according to the invention of breeding $B_1F_1$ hybrid (genome CAA) obtained by one time recurrent back-crossing Chinese cabbage (genome AA) to Hakuran (genome CCAA) which is the most usable in practice and $B_1F_1$ hybrid (genome CAC) obtained by one time recurrent back-crossing common cabbage (genome CC) to Hakuran (genome CCAA) in a mass seed production scale and applying these $B_1F_1$ hybrids to vegetable culture, will now be described in greater detail with reference to the accompanying drawings.

BRIEF DESCRIPTION OF THE DRAWINGS

FIGS. 3A, 3B, 3C and 3D are front elevational views showing shape of outside leaf of common cabbage and Chinese cabbage which are parents of Hakuran constituting material of $F_1$ hybrid plant according to the invention, of Hakuran obtained by such parents and of $B_1F_1$ plant obtained by back-crossing Chinese cabbage to Hakuran, leafstalk thereof being shown in section, FIG. 3A showing common cabbage, FIG. 3B showing Chinese cabbage, FIG. 3C showing Hakuran and FIG. 3D showing Hakuran × Chinese cabbage;

FIGS. 4A, 4B, 4C and 4D are front elevational views showing head leaf of common cabbage, Chinese cabbage, Hakuran and $B_1F_1$ plant, leafstalk thereof being shown in section, FIG. 4A showing common cabbage, FIG. 4B showing Chinese cabbage, FIG. 4C showing Hakuran and FIG. 4D showing Hakuran × Chinese cabbage;

FIGS. 5A, 5B, 5C, $5D_1$ and $5D_2$ are perspective views showing head, FIG. 5A showing common cabbage, FIG. 5B showing Chinese cabbage, FIG. 5C showing Hakuran, FIG. $5D_1$ showing Hakuran × 50 Chinese cabbage and FIG. $5D_2$ showing Hakuran × Rikidosan Chinese cabbage;

DESCRIPTION OF THE PREFERRED EMBODIMENTS

Figure 6:
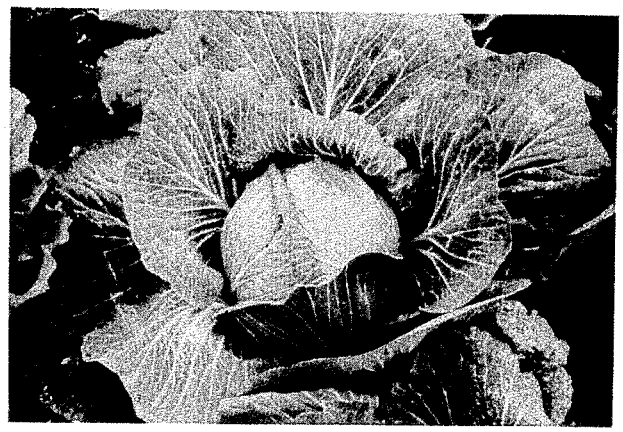
FIG. 6 is a photograph taken for Yoshin cabbage.
Figure 7:
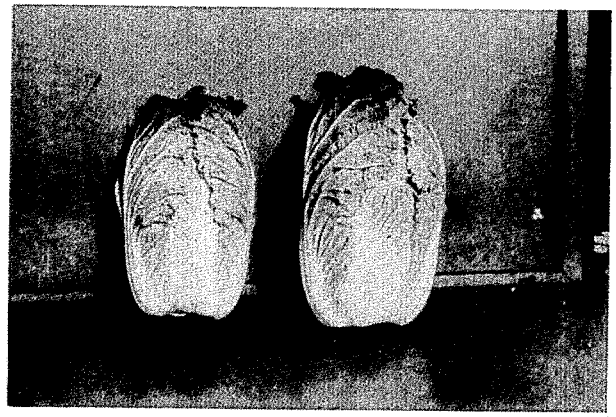
FIG. 7 is a photograph taken for Matsushima Pure No. 2 Chinese cabbage.

As material for Hakuran, use was made of allopolyploidy plant (genome CCAA) composed of interspecific hybrid (genome AC) formed of Yoshin cabbage (genome CC) (refer to FIG. 6) as female and Matsushima Pure No. 2 Chinese cabbage (genome AA) (refer to FIG. 7) as male. This allopolyploidy plant was obtained by immersing the seeds in 0.2% colchicine solution for 12 hours to 24 hours.

Figure 8:
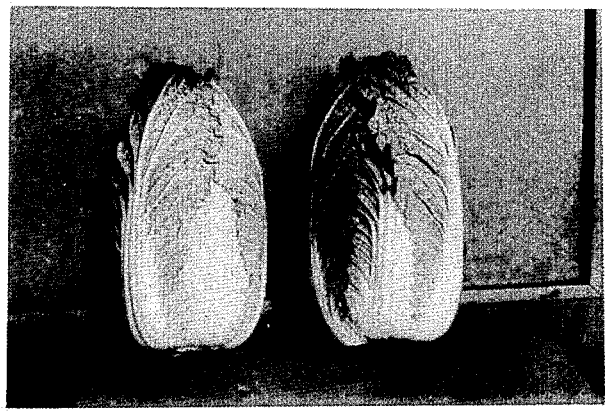
FIG. 8 is a photograph taken for Rikidosan Chinese cabbage.
Figure 9:
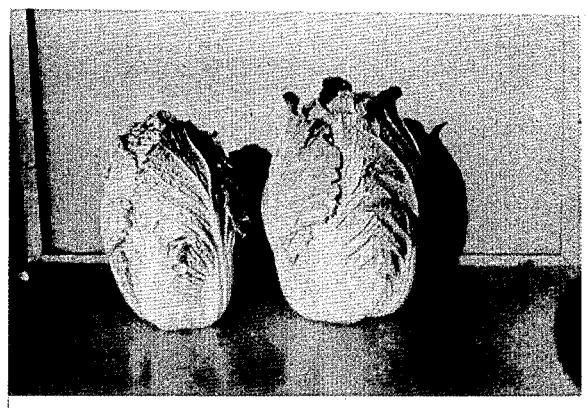
FIG. 9 is a photograph taken for 50 days Chinese cabbage.
Figure 10:
FIG. 10 is a photograph taken for Nozaki early cabbage.
Figure 11:
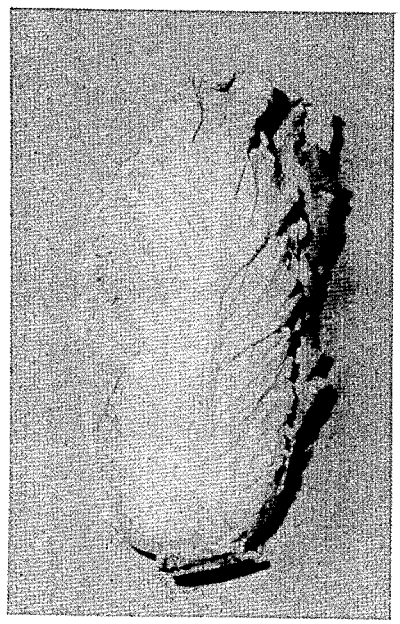
FIG. 11 is a photograph taken for allopolyploid (Yoshin cabbage × Matsushima Pure No. 2 Chinese cabbage) × Rikidosan Chinese cabbage ($CAA_1$), head thereof being shown.

As male for one time recurrent back-crossing, use was made of:

Rikidosan Chinese cabbage (genome $A_1A_1$) (refer to FIG. 8), 50 days Chinese cabbage (genome $A_2A_2$) (refer to FIG. 9), and Nozaki early cabbage (genome $C_1C_1$) (refer to FIG. 10)

to obtain $B_1F_1$ hybrid plants. That is,

Hakuran (CCAA) × Rikidosan Chinese cabbage ($A_1A_1$) = $CAA_1$ (refer to FIG. 11)

Hakuran (CCAA) × 50 days Chinese cabbage ($A_2A_2$) = $CAA_2$, and

Hakuran (CCAA) × Nozaki early cabbage ($C_1C_1$) = $CAC_1$

Comparison tests were effected in which these $B_1F_1$ hybrids ($CAA_1$, $CAA_2$) obtained by back-crossing the Chinese cabbage to the Hakuran and $B_1F_1(CAC_1)$ obtained by back-crossing the common cabbage to the Hakuran were compared with $F_1$ hybrid ($AA_1$) obtained by crossing the Chinese cabbage with each other and $F_1$ hybrid ($CC_1$) obtained by crossing common cabbages with each other.

The reasons why use was made of each $F_1$ hybrid of Chinese cabbage and common cabbage are as follows. These $F_1$ hybrids have come into wide use and the pure line does not have vigor, so that correct comparison could not be effected.

Figure 1:
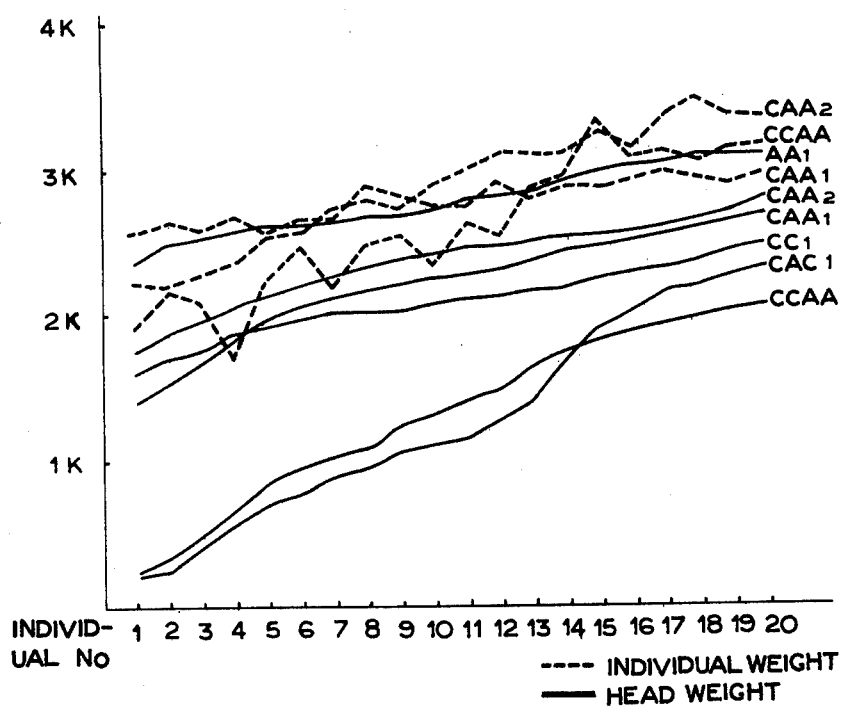
FIG. 1 is a graph showing individual weight and head weight of common cabbage ($CC_1$), Chinese cabbage ($AA_1$), Hakuran (CCAA) compared with those of $B_1F_1$ plants ($CAA_1$, $CAA_2$, $CAC_1$) obtained by one time recurrent back-crossing parent vegetables to Hakuran.

In FIG. 1, individual weight of the Hakuran, Chinese cabbage, common cabbage and the $B_1F_1$ hybrid obtained by back-crossing Chinese cabbage and common cabbage to the Hakuran is shown by dotted line curves and defined by total weight of head and outside leaf and the weight of outside leaf is defined by difference between the individual weight curve and a head weight curve shown by dotted lines. In addition, the head weight which is the weight of the head of the Hakuran and $B_1F_1$ hybrid is difficult to be discriminated from outside leaves thereof. All of these leaves whose head top is not closed, but is deviated from the vertical axial direction are defined as outside leaves. As seen in FIG. 1, the head weight of both $CAA_1$ and $CAA_2$ is slightly inferior to that of the Chinese cabbage, but is far superior to that of the Hakuran.

As will be described later, the outside leaves of the $B_1F_1$ hybrid ($CAA_1$, $CAA_2$) obtained by back-crossing the Chinese cabbage to the Hakuran are eatable and far heavier in individual weight inclusive of the outside leaves than the Hakuran.

In FIG. 1, uniformity is defined by an inclined angle of the head weight curve shown by full line with respect to the horizontal line. The smaller the inclined angle the better uniformity. As a result, the $B_1F_1$ hybrid is inferior in uniformity to the Chinese cabbage, but is far superior in uniformity to the Hakuran.

A good individual of the $B_1F_1$ hybrid ($CAC_1$) obtained by back-crossing the common cabbage to Hakuran is better in a rate of forming head than the Hakuran, but is inferior in uniformity to the Hakuran. Both the rate of forming head and the uniformity of the $B_1F_1$ hybrid ($CAC_1$) are inferior to those of the common cabbage and of the Hakuran.

(2) SEED YIELD IN THE CASE OF CROSSING HAKURAN WITH OTHER VEGETABLES

In the following Table 1 is shown cross compatibility of the Hakuran used as female and various species in Brassica genus used as male. It is possible to obtain a number of combinations with sufficiently large seed yield.

TABLE 1

SELF AND CROSS COMPATIBILITY OF HAKURAN AND OTHER SPECIES IN BRASSICA

| Name | Chromosome Number | Genome | ♀ \ ♂ | Hakuran | Brassica Napus | Kale type Chinese cabbage (SANTOSAI) | Kale type Chinese cabbage (KOMATSUNA) | Turnip (KANAMACHI) | Kale type Chinese cabbage (MIZUNA) | 50 days Chinese cabbage | Rikidosan Chinese cabbage | Mustard | Broad leafed mustard | Nozaki cabbage | Yoshin cabbage |
|---|---|---|---|---|---|---|---|---|---|---|---|---|---|---|---|
| B. napus | n=19 | CCAA+ | Hakuran Rape | X | O | O | O | O | O | O | O | O | O | O | O |
| B. Chinensis | n=19 | AACC |  |  | O | X | X | X | X | X | X | X | X | X | X |
| | n=10 | AA | Kale type Chinese cab. (SANTONA) |  | O | O | O | X | O | O | O | X | X | X | X |
| B. rapa | n=10 | AA | Kale type Chinese cab. (KOMATSUNA) |  |  |  | O |  |  |  |  |  |  |  |  |
| B. rapa | n=10 | AA | Turnip (KANAMACHI) |  |  |  |  | O | O | O | O | X | X | X | X |
| B. japonica | n=10 | AA | Kale type Chinese cab. (MIZUNA) |  |  |  |  |  | O | O | O | X | X | X | X |
| B. pekinensis | n=10 | AA | 50 days Chinese cabbage |  |  |  |  |  |  | O | O | X | X | X | X |
| B. pekinensis | n=10 | AA | Rikidosan Chinese cab. |  |  |  |  |  |  |  | O | X | X | X | X |
| B. juncea | n=10 | AABB | Mustard |  |  |  |  |  |  |  |  | X | X | X | X |
| B. juncea | n=18 | AABB | Broad Leafed mustard |  |  |  |  |  |  |  | O | O | O | X | X |
| B. oleracea | n=9 | CC | Nozaki cabbage |  |  |  |  |  |  |  |  |  |  | O | O |
| B. oleracea | n=9 | CC | Yoshin cabbage |  |  |  |  |  |  |  |  |  |  | O | O |

Note:
O compatible
X incompatible
+Genome of Hakuran is inclusive of CCAA and AACC. Natural allopolyploids of Brassica napus and Brassica juncea (mustard, broad leafed mustard) are self-compatible, so that repeated selfings do not lead to complete self incompatibility line. On the contrary, almost all of Hakurans which are artificial allopolyploids are self incompatible from the start.

Figure 2:
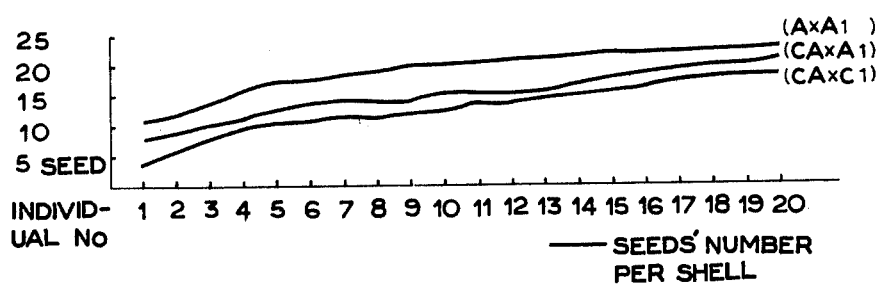
FIG. 2 is a graph showing the number of seeds per shell of $F_1$ hybrid plant (A × $A_1$) obtained by crossing Chinese cabbages with each other, of Hakuran × Chinese cabbage (CA × $A_1$) and of Hakuran × common cabbage (CA × $C_1$) and comparing these numbers with each other.

FIG. 2 is a graph of seed yield of $B_1F_1$ hybrid (CA × $A_1$) obtained by one time recurrent back-crossing the most practically usable Chinese cabbage to the Hakuran and $B_1F_1$ hybrid (CA × $C_1$) obtained by one time recurrent back-crossing the common cabbage to the Hakuran on the one hand and the seed yield of $F_1$ hybrid ($AA_1$) of the Chinese cabbage on the other hand. As seen from FIG. 2, the seed yield of the $B_1F_1$ hybrid is slightly smaller in the number of seeds per shell than the seed yield of the $F_1$ hybrid of Chinese cabbage, but the $B_1F_1$ hybrid is sufficiently usable in practice.

In practice, seeds are obtained from the female Hakuran only, so that alternate planting of male and female results in one-half the seed yield of the Chinese cabbage. The use of 2 female ridges and 1 male ridge ensures 2/3 times the seed yield of the Chinese cabbage. If the ridge width is shortened by 30% and after blooming the male is cut, it is possible to obtain a seed yield which is substantially equal to that of the Chinese cabbage.

In the case of obtaining seeds, care must be taken that since the Hakuran can cross with almost all of species in Brassica as shown in Table 1, the seed field must strictly be isolated and prevented from crossing Brassica except the male species.

(3) SHAPE AND PROPERTY OF $F_1$ HYBRID PLANT ACCORDING TO THE INVENTION

As shown in FIG. 1, the seed yield and uniformity of the $F_1$ hybrid plant according to the invention are slightly inferior to those of the Chinese cabbage and the common cabbage, but are generally superior to those of the Hakuran.

The shape of the $F_1$ hybrid plant according to the invention becomes more or less different depending on the kind of common cabbage and Chinese cabbage constituting allopolyploid and with the kind of Chinese cabbage used for one time recurrent back-crossing. The outside leaf and head leaf have a length of approximately 40 cm to 60 cm and width of approximately 25 cm to 30 cm. The Hakuran has a shape which is intermediate between the shape of the common cabbage and the shape of the Chinese cabbage. On the contrary, the shape of the $F_1$ hybrid plant according to the invention is nearly equal to that of the Chinese cabbage. The $F_1$ hybrid plant according to the invention is shorter in leafstalk, wider in width and thinner in thickness than the common cabbage and Hakuran. In addition, lobations produced at the lower part of the leaf blade are less than those of the common cabbage and Hakuran and nearly equal to those of the Chinese cabbage as shown in FIGS. 3A to 3D and 4A to 4D.

The shape of head becomes different depending on the kind of the common cabbage and Chinese cabbage used for the allopolyploid and $B_1F_1$ hybrid of one time recurrent back-crossing.

The $B_1F_1$ hybrid plant shown in FIG. $5D_2$ and obtained by back-crossing Rikidosan Chinese cabbage to allopolyploid of Yoshin cabbage and Matsushima Pure 2 Chinese cabbage has a tall head. The shape of head of the $B_1F_1$ hybrid plant shown in FIG. $5D_1$ and obtained by back-crossing 50 days Chinese cabbage to allopolyploid of Yoshin cabbage and Matsushima Pure 2 Chinese cabbage is nearly equal to that of the Chinese cabbage. In FIGS. 5A to $5D_2$ is shown the shape of heads.

The taste of the $B_1F_1$ hybrid plant according to the invention cannot be expressed by numerals, $CAA_1$, $CAA_2$ are crisper than the Hakuran and have no pungent flavor inherent to the common cabbage and are very sweet.

The $B_1F_1$ hybrid plant according to the invention is generally crisper than the Chinese cabbage and softer than the common cabbage. The $B_1F_1$ hybrid plant is not pungent contrary to the common cabbage and Hakuran, but is always sweet and particularly sweet inside thereof.

The $B_1F_1$ hybrid plant according to the invention may be utilized for all of the use of the Chinese cabbage, common cabbage, lettuce, celery and Hakuran.

(4) COOKING

The leaf blade of the outside leaf of the $B_1F_1$ hybrid is cut into fine pieces. These pieces added to Gyoza show less contraction.

The leaf blade and leafstalk of the outside leaf of the $B_1F_1$ hybrid are slightly larger in thickness than the Chinese cabbage, so that these parts are sliced off and sliced pieces thus obtained may be pickled with salt and rice bran and also pickled with salt water, vinegar, roller leaf, garlic, etc. to produce Russian pickles.

In case of pickling with salt and rice bran, the salt ingredient is penetrated into the sliced pieces at a rate slower than the Chinese cabbage by one day, so that the pickles obtained two days after pickling are good for eating.

The leafstalk of the outside leaf of the $B_1F_1$ hybrid is sliced off into stick-shaped pieces which may be tasted with or without cooking.

The head leaf of the $B_1F_1$ hybrid may be pickled in the same manner as in the case of the outside leaf and may also be boiled in a pan or fried in oil. There is no risk of the head leaf being too softened by boiling which has been encountered with the Chinese cabbage.

The head leaf of the $B_1F_1$ hybrid may be cut into fine pieces as in the case of the cabbage or may be torn into large pieces like lettuce which may be tasted by putting dressing, mayonnaise sauce, soy and the like thereon. The Chinese cabbage could not be tasted without cooking as it is fishy and the common cabbage is hard. On the contrary, the $B_1F_1$ hybrid plant according to the invention is very crisp and very delicious.

The central part of the head of the $B_1F_1$ hybrid according to the invention is extremely brittle, so that it may be divided in its lengthwise direction into stick-shaped pieces which may be tasted together with table salt without cooking in the same manner as in the case of celery without sweet smell.

(5) VEGETABLE CULTURE OF $B_1F_1$ HYBRID PLANT ACCORDING TO THE INVENTION

Vegetable culture of the $B_1F_1$ hybrid plant obtained by allopolyploid (cabbage × Chinese cabbage) × Chinese cabbage may be effected substantially in the same manner as in the case of the Chinese cabbage. But, the $B_1F_1$ hybrid plant is partly possessed of the property of the common cabbage, so that the vegetable culture thereof becomes more or less different from that of the Chinese cabbage.

(I) Seed Sowing

A growing term of the $B_1F_1$ hybrid is shorter than that of the common cabbage, but longer than that of the Chinese cabbage. In and around Tokyo, in the case of autumn-sown and early winter-harvesting, if the seeds are sown on 20th of August, it is possible to harvest the $B_1F_1$ hybrid plant in latter part of November to upper part of December. The growing term is about 90 days and after that term harvesting of the $B_1F_1$ hybrid plant may be started. In South Japan, it is relatively warm in winter, so that the seeds are sown on the 10th of September and it is possible to harvest the $B_1F_1$ hybrid plant from the latter part of December to the latter part of February of the next year.

In cold countries, the seeds are sown from the latter part of July to the upper part of August and the $B_1F_1$ hybrid may be started to be harvested from the upper part of November to the middle part of November.

In the case of spring-sown, use may be made of the common cabbage and Chinese cabbage for constituting the Hakuran and belonging to slow bolting cultivar and of the Chinese cabbage used for one time recurrent back-crossing and belonging to slow bolting cultivar. For example, it is preferable to use allopolyploid (Nozaki early cabbage cultivar × Nozaki spring sown Chinese cabbage) × Nozaki spring sown Chinese cabbage.

(II) Seedbed

The seed of the $B_1F_1$ hybrid according to the invention may directly be sown. The initial growing of the $B_1F_1$ hybrid is slightly slower than that of the Chinese cabbage, so that it is preferable to sow the seed in compost block, peat moss block, etc. and transplant the young plant. As in the case of the Chinese cabbage, the compost block may be composed of a mixture consisting of a compost and a field soil in two equal parts. The mixture is added with 150 gr of ammonium phosphate 14 per 3.3 $m^2$ and water and the whole is kneaded. The kneaded mixture is put into a wooden container having a thickness of 6 cm to 9 cm and a width of 1 m. The container is closed with a cover. When the compost block in the container becomes dried into a solid body whose hardness is nearly equal to that of sweet paste, the compost block is divided into square bodies with sides of 10 cm. At the center of the square body is formed a hole having a depth of about 6 mm by means of a bar. Into the hole are sown 3 to 4 seeds and then the hole is closed with covering soil. After the seeds have been germinated, thinning is effected to make adjacent plants independent one from the other.

(III) Field

After tillage and soil preparation, a groove having a width of 75 cm in the case of uni-ridge and a groove having a width of 150 cm in the case of double ridge are formed in the field. These grooves are added with basal fertilizer consisting of 2 tons of compost and 120 kg of calcium magnesia as well as with chemical manure consisting of 35 kg of N, 18 kg of P and 35 kg of K10$a$. Then, these grooves are filled up with soil to form a ridge having a height of about 10 cm. Young plants are transplanted on one side of the compost and are spaced apart from each other by about 50 cm to 80 cm.

During the vegetable culture, side dressing fertilizer is added 4 times. Immediately after the first transplant, the side dressing fertilizer composed of water containing 5 kg of ammonium nitrate per 10$a$ of the field dissolved therein is added. The same amount of water with ammonium nitrate is added two times up to the beginning of the formation of head. Fourth, at the beginning of the formation of head, 7 kg to 10 kg of ammonium nitrate and 10 kg of potassium chloride per 10$a$ of the field are added.

(IV) Plant Disease and Noxious Insect

The $B_1F_1$ hybrid plant according to the invention is more resistant than the Chinese cabbage against the plant disease such as ring rot virus, erwinia rot, etc., but is not absolutely resistant against such disease. As a result, the $B_1F_1$ hybrid is prevented against such disease by spraying a solution which contains 0.1% (1/1000) Daisen. Aphides are driven away from the $B_1F_1$ hybrid plant by spraying a solution which contains 0.03% (1/3000) Marason.

(V) Harvesting

The harvesting of the $B_1F_1$ hybrid according to the invention is effected at times which are more or less different in accordance with the kinds thereof. In general, the harvesting is effected at times which are later than the seed sowing by 80 days to 100 days. In the first place, the $B_1F_1$ hybrid plant whose head is firmly tightened is harvested.

The $B_1F_1$ hybrid having complete heading must not be left on the field for a long because the head splits during raining. As described above with reference to the use of the $B_1F_1$ hybrid, the outside leaf thereof can be tasted contrary to the Chinese cabbage and common cabbage, so that 3 to 4 outside leaves located at the outside are removed and most of the outside leaf bundled together with the head leaf may be shipped.

As described above, the present invention cannot only improve an interspecific plant composed of Brassica oleracea L and another Brassica genus, i.e., a so-called Hakuran so as to further improve its quality but also make varieties thereof high in uniformity and increase the seed yield. Thus, the invention contributes greatly in vegetable culture.

What is claimed is:

1. A method of breeding new varieties of a first filial generation plant which comprises: crossing a self-incompatible allopolyploidy plant as female with a plant of Brassica species having genomes AA, AACC or AABB as male and which is cross compatible with said female, said allopolyploidy plant being obtained by immersing the seeds of an interspecific plant formed by crossing a plant of Brassica species with a different plant of Brassica species, said species having genomes CC and AA in colchicine solution, and said Brassica species having a chromosome number which is smaller than that of said allopolyploidy plant, and collecting the seeds of said first filial generation plant.

2. The method according to claim 1, wherein said allopolyploidy plant is composed of a reciprocal cross plant formed between said Brassica species.

3. The method according to claim 1, wherein said allopolyploidy plant has genomes AACC.

4. The method according to claim 3, wherein said allopolyploidy plant is a Hakuran composed of Chinese cabbage and common cabbage and said Brassica species as male, is a Chinese cabbage, said first filial generation plant having genomes CAA.

* * * * *